United States Patent [19]
Larsen et al.

[11] Patent Number: 5,851,214
[45] Date of Patent: Dec. 22, 1998

[54] SURGICAL INSTRUMENT USEFUL FOR ENDOSCOPIC PROCEDURES

[75] Inventors: Scott W. Larsen; Christopher McDonnell, both of Newtown; Scott W. Reed, Shelton, all of Conn.

[73] Assignee: United States Surgical Corporation, Norwalk, Conn.

[21] Appl. No.: 713,091

[22] Filed: Sep. 16, 1996

Related U.S. Application Data

[63] Continuation of Ser. No. 320,478, Oct. 7, 1994, abandoned.

[51] Int. Cl.$^6$ ..................................................... A61B 17/32
[52] U.S. Cl. .......................... 606/170; 606/162; 606/205; 606/208
[58] Field of Search ................................ 606/79, 83, 167, 606/170, 174, 205, 207, 206, 208; 128/749, 751, 753, 754

[56] References Cited

U.S. PATENT DOCUMENTS

| Re. 33,258 | 7/1990 | Onik et al. ................................. 604/22 |
| 3,814,102 | 6/1974 | Thal . |
| 4,084,594 | 4/1978 | Mosior . |
| 4,122,856 | 10/1978 | Mosior et al. . |
| 4,201,213 | 5/1980 | Townsend . |

(List continued on next page.)

FOREIGN PATENT DOCUMENTS

| 0381096 | 12/1907 | France ..................................... 606/207 |
| 2808911 | 3/1979 | Germany . |
| 9307621 | 7/1993 | Germany . |
| 4341734 | 9/1994 | Germany . |
| WO 9400059 | 1/1994 | WIPO . |

OTHER PUBLICATIONS

Orthopedic Surgical Instruments, George Teimann & Co., 1994.
Circon Sales Brochure for Reposable Laparoscopy Instruments, 1993.
Storz Sales Brochure for the World of Endoscopy, 4th Edition/90.
Ethicon Endo–Surgery Sales Brochure, pp. 18–20.
Cooper Endoscopy Brochure for Laparoscopic Instruments with Replaceable Distal Jaws, 1993.
Optima ™ Sales Brochure for The Endoscopic Hand Instrument of Choice, 1993.
Codman Sales Literature for Endoscopic Instruments.
Pilling Instruments Sales Literature for Cardiovascular, Thoracic and General Surgical Instruments, pp. 164,165.
Koros Sales Literature for Introducing the Latest Advancement in Laproscopy, Endoscopy, Thoracoscopy Instruments, 1992.
Storz Sales Literature on Take–Apart ® Instruments
Zimmer Sales Literature, 1966.

*Primary Examiner*—Micheal Powell Buiz
*Assistant Examiner*—Daphna Shai

[57] ABSTRACT

The present application discloses instruments for use in an endoscopic discetomy procedure which are configured to be disassembled for cleaning and reassembled for subsequent utilization. The preferred embodiments include endoscopic rongeur-style instruments which may be used to remove calcification, to trim away part of a bone and to remove tissue and tissue samples for biopsy purposes.

The endoscopic surgical instruments of the present application are provided with a handle mechanism, an elongated endoscopic portion extending from the handle mechanism and a tool mechanism supported at a distal end of the endoscopic portion. The handle mechanism includes a body portion having an upper and a lower body portion, a stationary grip extending from the body portion and a pivotable grip pivotally mounted to body portion. In one embodiment, the pivotable grip is detachably mounted to body portion by a locking member which includes a fastener having a rod and an abutment portion. The endoscopic portion includes a first half-section member and a second half-section member which is preferably removably mounted to the first half-section member and is slidable with respect thereto.

24 Claims, 15 Drawing Sheets

U.S. PATENT DOCUMENTS

| | | | |
|---|---|---|---|
| 4,243,047 | 1/1981 | Olsen | 128/751 |
| 4,282,884 | 8/1981 | Boebel | 128/751 |
| 4,369,788 | 1/1983 | Goald . | |
| 4,440,170 | 4/1984 | Golden et al. . | |
| 4,545,374 | 10/1985 | Jacobson . | |
| 4,569,131 | 2/1986 | Falk et al. . | |
| 4,722,338 | 2/1988 | Wright et al. . | |
| 4,733,663 | 3/1988 | Farley . | |
| 4,777,948 | 10/1988 | Wright . | |
| 4,990,148 | 2/1991 | Worrick, III et al. | 606/83 |
| 5,009,661 | 4/1991 | Michelson | 606/170 |
| 5,026,375 | 6/1991 | Linovitz et al. | 606/79 |
| 5,176,699 | 1/1993 | Markham . | |
| 5,195,541 | 3/1993 | Obenchain . | |
| 5,242,439 | 9/1993 | Larsen et al. | 606/15 |
| 5,269,797 | 12/1993 | Bonati et al. | 606/170 |
| 5,273,519 | 12/1993 | Koros et al. | 606/83 |
| 5,282,800 | 2/1994 | Foshee et al. | 606/52 |
| 5,304,203 | 4/1994 | El-Mallawany et al. | 606/207 |
| 5,308,358 | 5/1994 | Bond et al. | 606/205 |
| 5,312,407 | 5/1994 | Carter | 606/79 |
| 5,313,962 | 5/1994 | Obenchain . | |
| 5,336,238 | 8/1994 | Holmes et al. | 606/208 |
| 5,342,391 | 8/1994 | Foshee et al. | 606/205 |
| 5,368,606 | 11/1994 | Marlow et al. | 606/170 |
| 5,385,570 | 1/1995 | Chin et al. | 606/170 |
| 5,451,227 | 9/1995 | Michaelson | 606/170 |

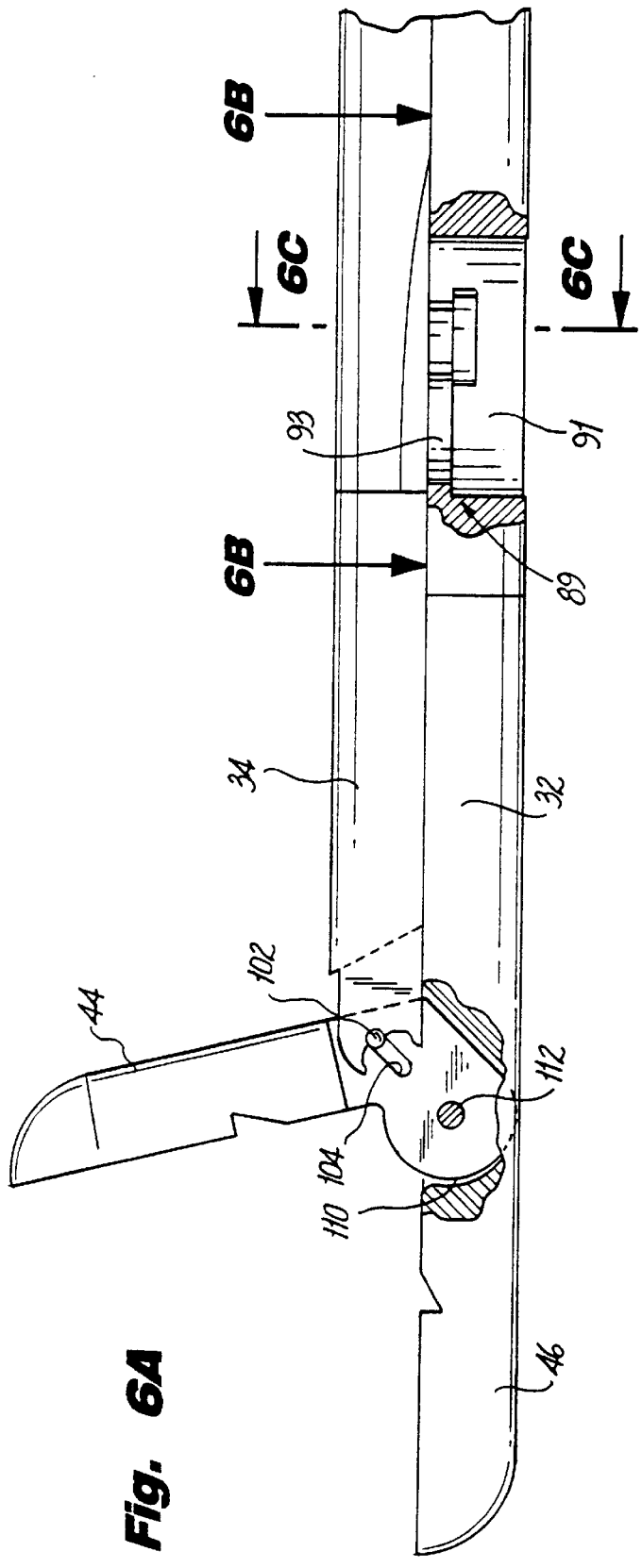
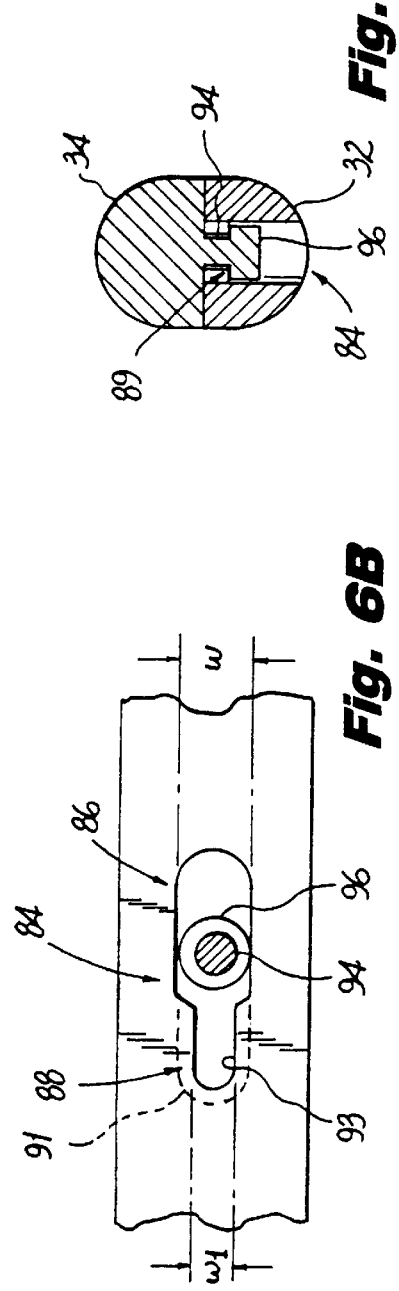
Fig. 6A
Fig. 6B
Fig. 6C

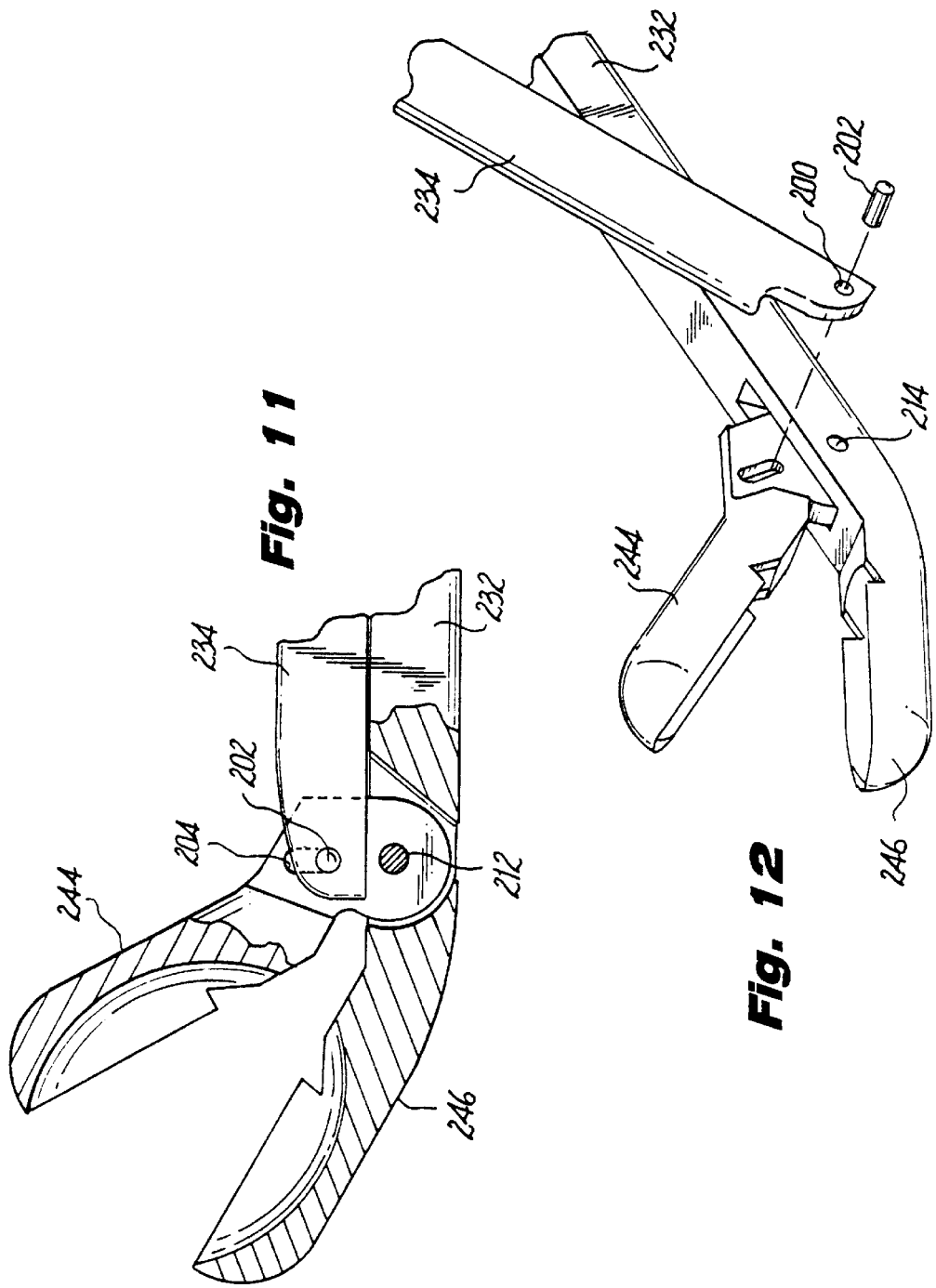

SURGICAL INSTRUMENT USEFUL FOR ENDOSCOPIC PROCEDURES

This is a continuation of application Ser. No. 08/320,478 filed on Oct. 7, 1994, now abandoned.

BACKGROUND

1. Technical Field

The present application relates to surgical instruments and, more particularly, to endoscopic surgical instruments useful to perform endoscopic discectomy procedures and other minimally invasive spinal procedures.

2. Background of the Related Art

Back pain is a common affliction affecting millions of people. In many instances, back pain is caused by a herniated intervertebral disc. Intervertebral discs are generally cylindrical-shaped structures corresponding to the margins of the adjacent vertebrae. An outer ring known as the annulus fibrosus composed of concentric layers of fibrous tissue and fibrocartilage surrounds a cartilage-like core known as the nucleus pulposus. When an intervertebral disc is herniated, the softer nucleus projects through a torn portion of the annulus, creating a bulge which extends beyond the intervertebral foramen. As a result of the bulging disc, various spinal nerves may be compressed, causing pain or numbness.

Various procedures are used to treat herniated intervertebral discs. In mild disc herniation, pressure on adjacent nerves is lessened through non-surgical techniques. Such techniques include drugs (analgesics, anti-inflammatory drugs, muscle relaxants), physical therapy, and rest. If these non-surgical approaches are not successful, surgical intervention is necessary. Various surgical procedures have been developed to remove at least a portion of the herniated disc. Such procedures include laminotomies, laminectomies, percutaneous discectomy and a newly developed procedure for performing a laparoscopic discetomy.

In larninotomy (also referred to as interlaminar exploration), a posterior approach is used to access the spine through a longitudinal incision. Small amounts of the bony spinal lamina are removed, allowing access to, and removal of, portions of the herniated nucleus pulposus.

Laminectomy is a surgical procedure which, like laminotomy, uses a posterior approach to the herniated disc. In laminectomy, a larger portion of the spinal lamina or laminae are removed to access and remove portions of a herniated disc nucleus. Because both laminotomy and laminectomy require removal of bone and retraction of nerves and muscles, hospitalization and recuperation periods are lengthy. Additionally, removal of bone may lead to future spinal instability.

To minimize the need to remove portions of the vertebrae, other approaches to the herniated disc have been used. In particular, percutaneous discectomy employs a posterolateral approach. Instruments are inserted through a cannula inserted through the patient's side. The disc annulus is pierced and the herniated nucleus is mechanically disintegrated, the pieces being removed through suction. This technique is shown for example in U.S. Pat. Nos. 4,545,374, 5,242,439 and RE 33,258.

Endoscopic surgery involves incising through body walls via small incisions, generally by use of a trocar having a obturator with a sharp tip removably positioned in a cannula. After penetration, the obturator is removed leaving the cannula positioned in the body for reception of a camera or endoscope to transmit images to a remote TV monitor. Specialized instruments such as forceps, cutters, and applicators are inserted through other trocar sites for performing the surgical procedure while being viewed by the surgeon on the monitor. U.S. Pat. Nos. 5,195,541 and 5,313,962 disclose a method for performing a laparoscopic lumbar discetomy in which an anterior approach is utilized to access the spine.

Traditionally, endoscopic instruments have been manufactured as reusable devices which can be cleaned and sterilized following a procedure, or as disposable devices which are discarded after a single surgical procedure. With disposable devices cleaning is not an issue since they are not reused or resterilized. Reusable instruments must, however, be cleaned and properly sterilized after each surgical procedure. Although techniques such as steam sterilization have been widely used, they are often inadequate to reach all of the blood and tissue residues that can enter a surgical instrument during a surgical procedure. Since endoscopic instruments are often constructed with an elongated tubular body housing and small mechanical parts, blood and tissue which infiltrates a endoscopic instrument's body can be particularly difficult to remove. Thus, endoscopic reusable instruments are often difficult to clean.

The benefits of reusable endoscopic instruments that can be disassembled for cleaning following a surgical procedure and thereafter reassembled for subsequent utilization have long been recognized. Once disassembled, access to the interior portions of the instrument body and the internal mechanical elements housed therein becomes easier. As a result, traditional cleaning and sterilization methods become more reliable.

An example of surgical instrument that can be disassembled for improved cleaning is disclosed in U.S. Pat. No. 5,308,358 to Bond et al. The Bond et al. patent describes a device having a threaded coupling for connecting the body of the instrument to the handle assembly, and a similar threaded arrangement for connecting the tool assembly to the distal end of the instrument body. Over time however, threaded connections such as these at the tool assembly end can become worn or damaged, due to its contact with body fluids, thereby preventing reassembly of the instrument. Furthermore, the instrument described in Bond et al. is not specifically adapted for discetomy procedures. In general, discetomy procedures require specialized instruments such as rongeurs which are available in a number of styles, two such styles being the cervical bone rongeur and the pituitary rongeur, both of which are known in the art. These instruments are used to remove calcification, to trim away part of a bone and to remove tissue and tissue samples for biopsy purposes.

An example of a discetomy surgical instrument which can be disassembled for cleaning is disclosed in U.S. Pat. No. 5,273,519 to Koros et al. The Koros et al patent discloses a device which can be at least partially disassembled for cleaning. The instrument disclosed, however, includes several small mechanical parts. As discussed above, small mechanical parts can make blood and tissue which infiltrates a endoscopic instrument particularly difficult to remove.

With the advent of endoscopic surgery and the recognition of its advantages over open procedures in reducing costs by shortening the patient's hospital stay and time of recovery so the patient can resume normal activity sooner, the industry has been viewing endoscopic discectomy as an alternative to the other techniques and surgical methods described above. Therefore, the need exists for endoscopic instrumentation which can remove portions of tissue and bone during an endoscopic discetomy procedure while being configured for easy and reliable disassembly for cleaning and subsequent reassembly for utilization.

SUMMARY

The present application discloses instruments for use in an endoscopic discetomy procedure which are configured to be disassembled for cleaning and reassembled for subsequent utilization. The preferred embodiment include endoscopic rongeur-style instruments which may be used to remove calcification, to trim away part of a bone and to remove tissue and tissue samples for biopsy purposes.

More particularly the endoscopic surgical instruments of the present application are provided with a handle mechanism, an elongated endoscopic portion extending from the handle mechanism and a tool mechanism supported at a distal end of the endoscopic portion. The handle mechanism includes a body portion having an upper and a lower body portion, a stationary grip extending from the body portion and a pivotable grip pivotally mounted to the body portion. In one embodiment, the pivotable grip is detachably mounted to the body portion by a locking member which includes a fastener having a rod and an abutment portion. The endoscopic portion includes a first half-section member and a second half-section member which is preferably removably mounted to the first half-section member and is slidable with respect thereto.

BRIEF DESCRIPTION OF THE DRAWINGS

Various embodiments are described herein with reference to the drawings wherein:

FIG. 6A is an enlarged side plan view in partial cross-section of the distal end of the surgical instrument of FIG. 1.

FIG. 6B is a top view taken along line 6B—6B of FIG. 6A.

FIG. 6C is "a" cross-sectional view taken along line 6C—6C of FIG. 6A.

FIG. 11 is an enlarged side plan view in partial cross-section of the distal end showing the jaw mechanism of the instrument of FIG. 10.

FIG. 12 is an enlarged perspective view with parts separated of the distal end showing the jaw mechanism of the instrument of FIG. 10.

DETAILED DESCRIPTION OF THE PREFERRED EMBODIMENTS

Figure 1:
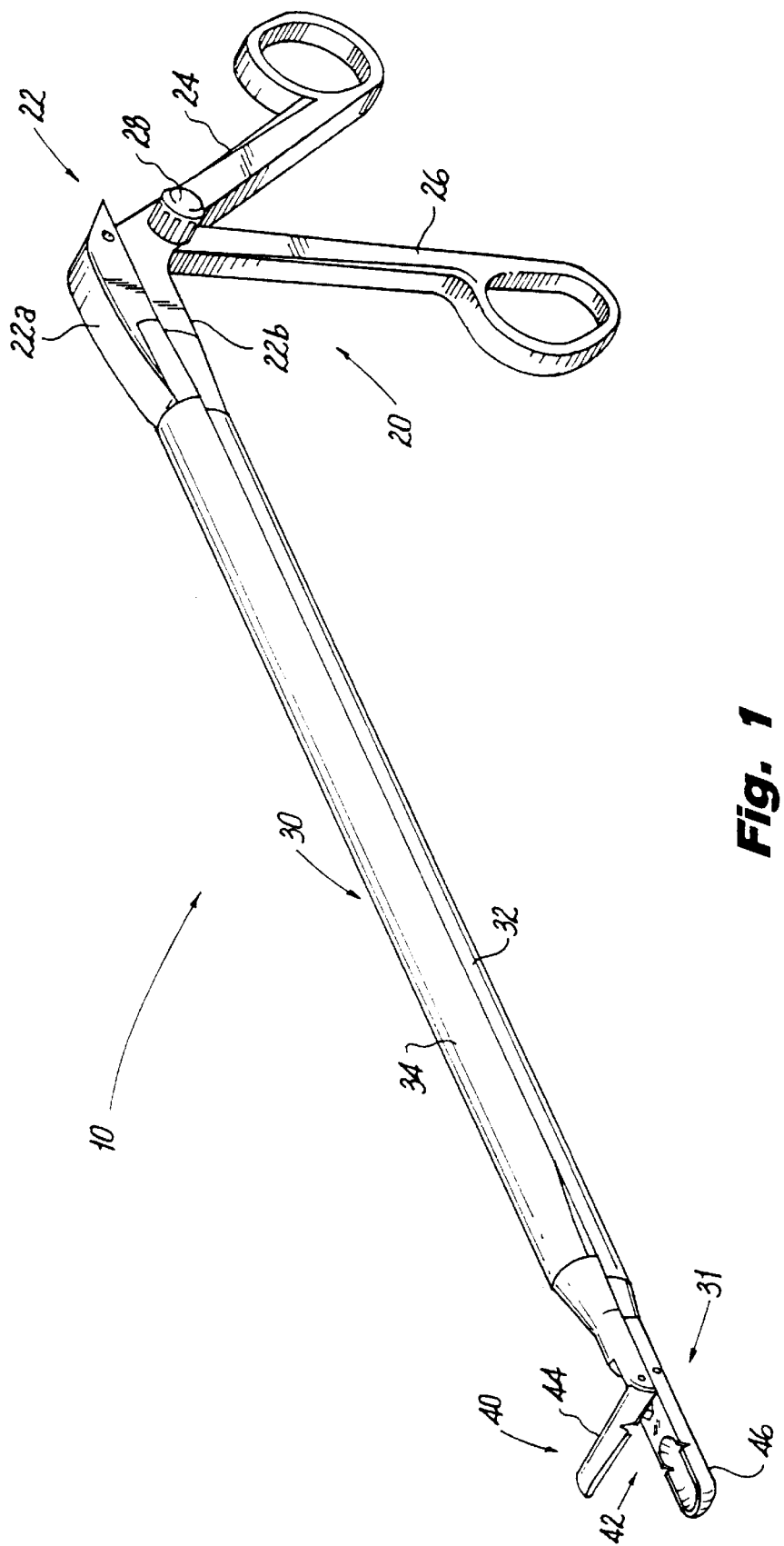
FIG. 1 is a perspective view of a first embodiment of an endoscopic surgical instrument for removing portions of tissue during an endoscopic discectomy procedure according to the present application.

Turning now to the drawings in detail in which like reference numerals identify similar or identical elements throughout the several views, FIG. 1 depicts an endoscopic surgical rongeur instrument 10 which may be used to remove portions of tissue during an endoscopic discectomy procedure and which is configured to be disassembled for cleaning and reassembled for subsequent utilization. In describing the surgical instruments of the present application, the term "proximal" refers to a direction of the instrument away from the patient and towards the user while the term "distal" refers to a direction of the instrument towards the patient and away from the user.

Instrument 10 includes a handle mechanism 20, an elongated endoscopic portion 30 extending from the handle mechanism 20 and a tool mechanism 40 supported at a distal end 31 of endoscopic portion 30. Handle mechanism 20 includes a body portion 22 having an upper 22a and a lower 22b body portion, a stationary grip 24 extending from body portion 22 and a pivotable grip 26 pivotally mounted to body portion 22. Pivotable grip 26 is detachably mounted to body portion 22 by locking member 28 which will be described in greater detail hereinbelow. Endoscopic portion 30 includes a first half-section member 32 and a second half-section member 34 which is preferably removably mounted to the first half-section member 32 and is slidable with respect thereto. Tool mechanism 40 includes jaw assembly 42 which in the embodiment of FIG. 1 includes an actuating jaw member 44 and a stationary jaw member 46.

Figure 2:
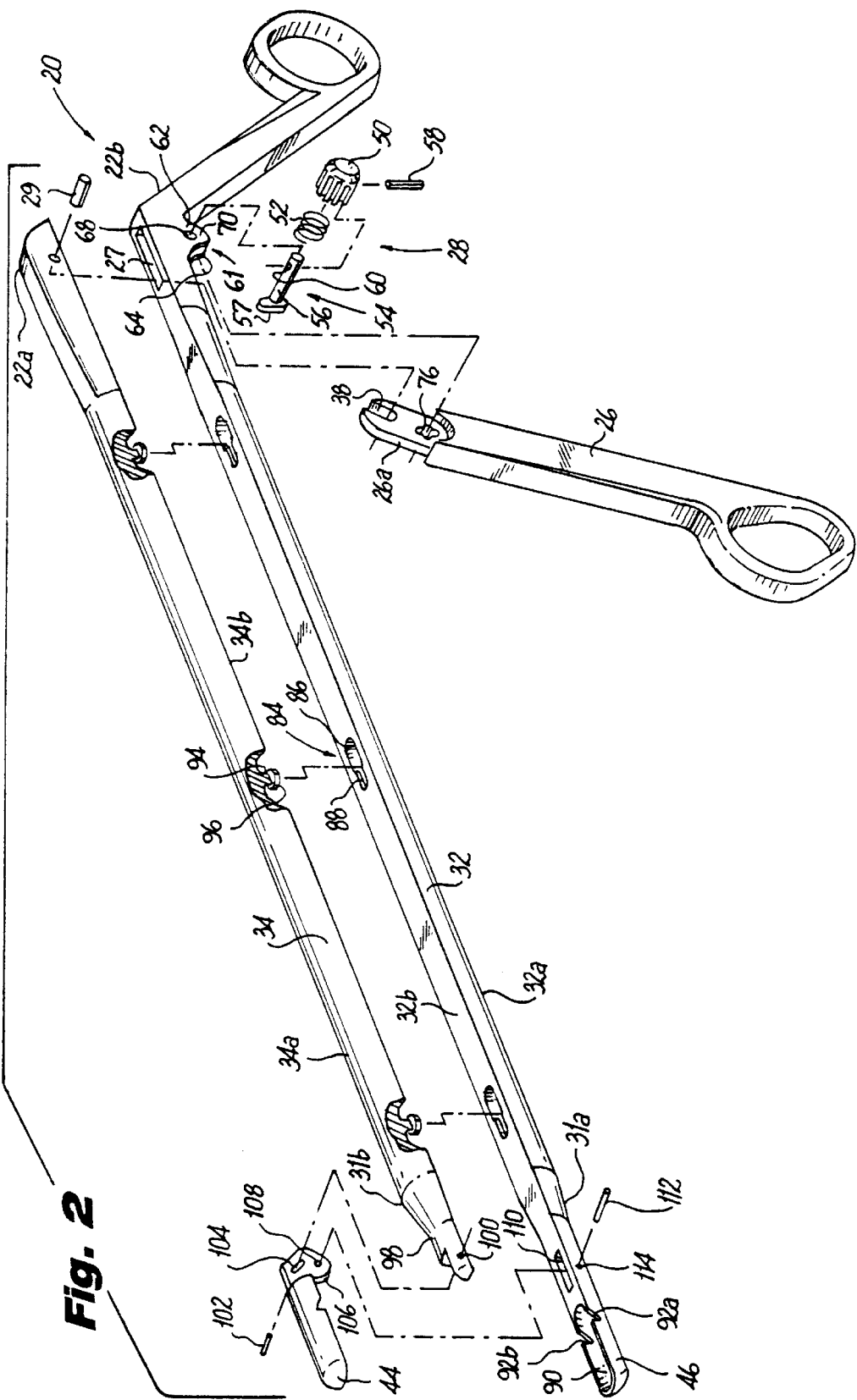
FIG. 2 is a perspective view with parts separated of the surgical instrument of FIG. 1.
Figure 7:
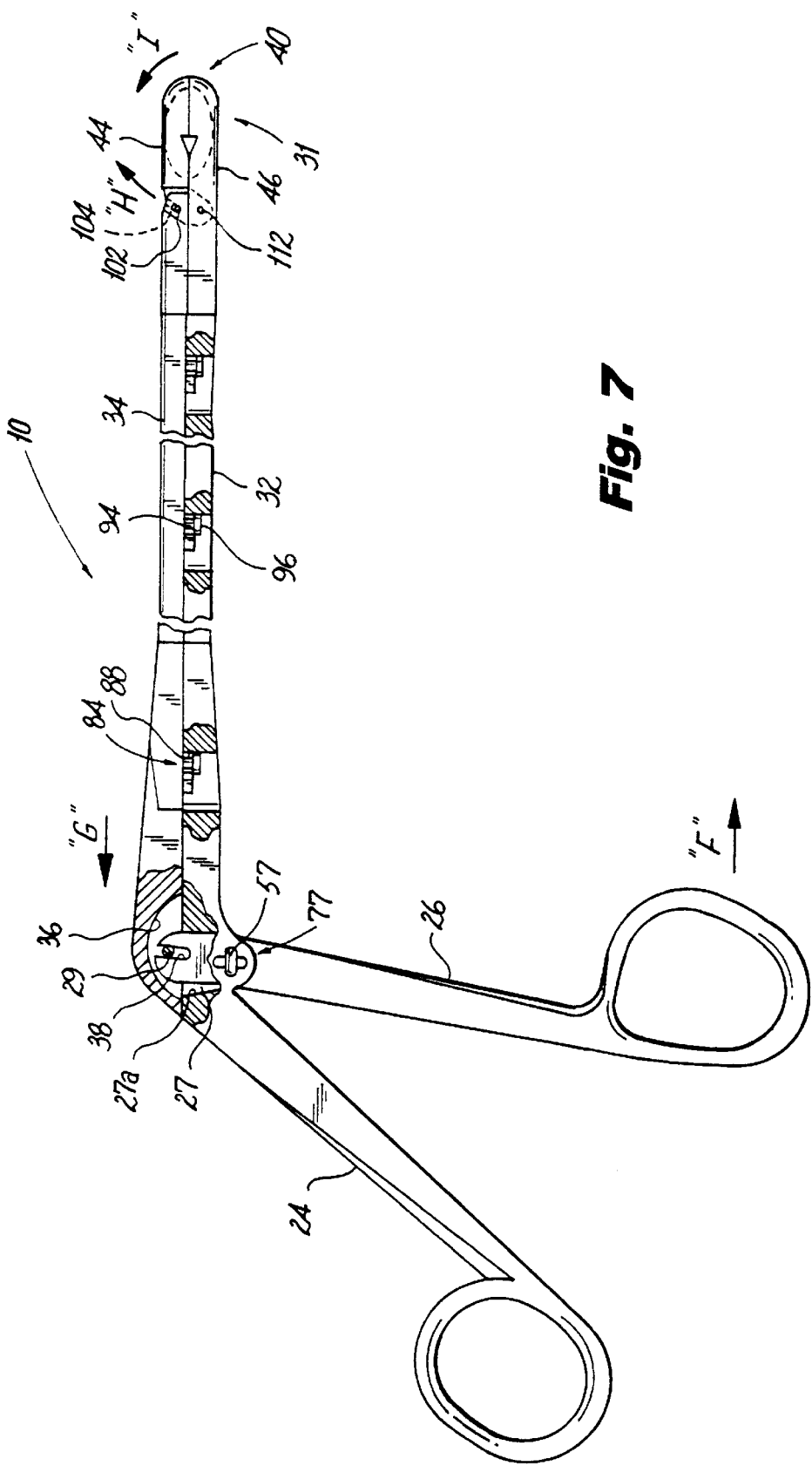
FIG. 7 is a side plan view in partial cross section of the instrument of FIG. 1 in a first position.
Figure 8:
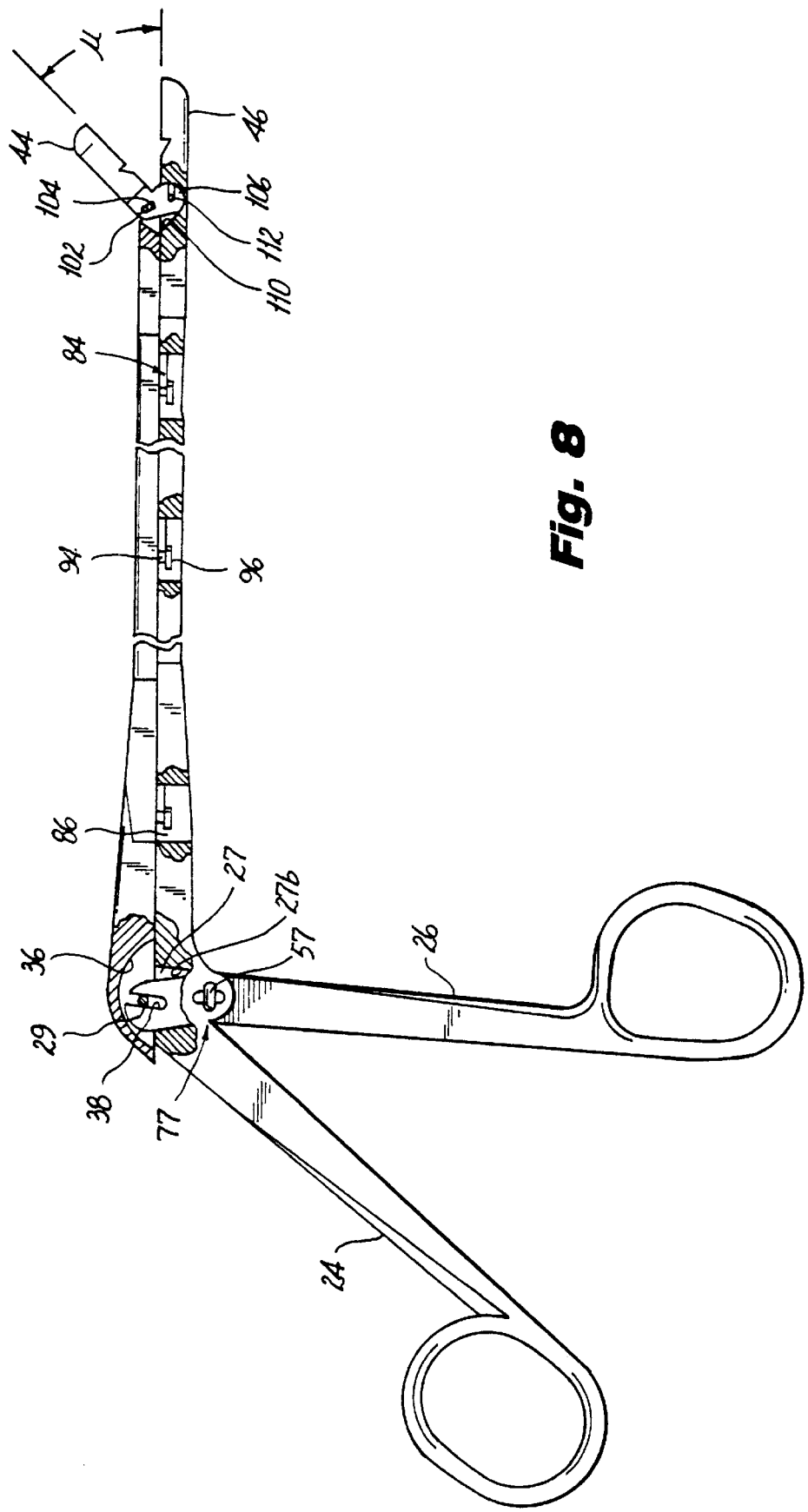
FIG. 8 is a side plan view in partial cross section of the instrument of FIG. 1 in a second position.
Figure 9:
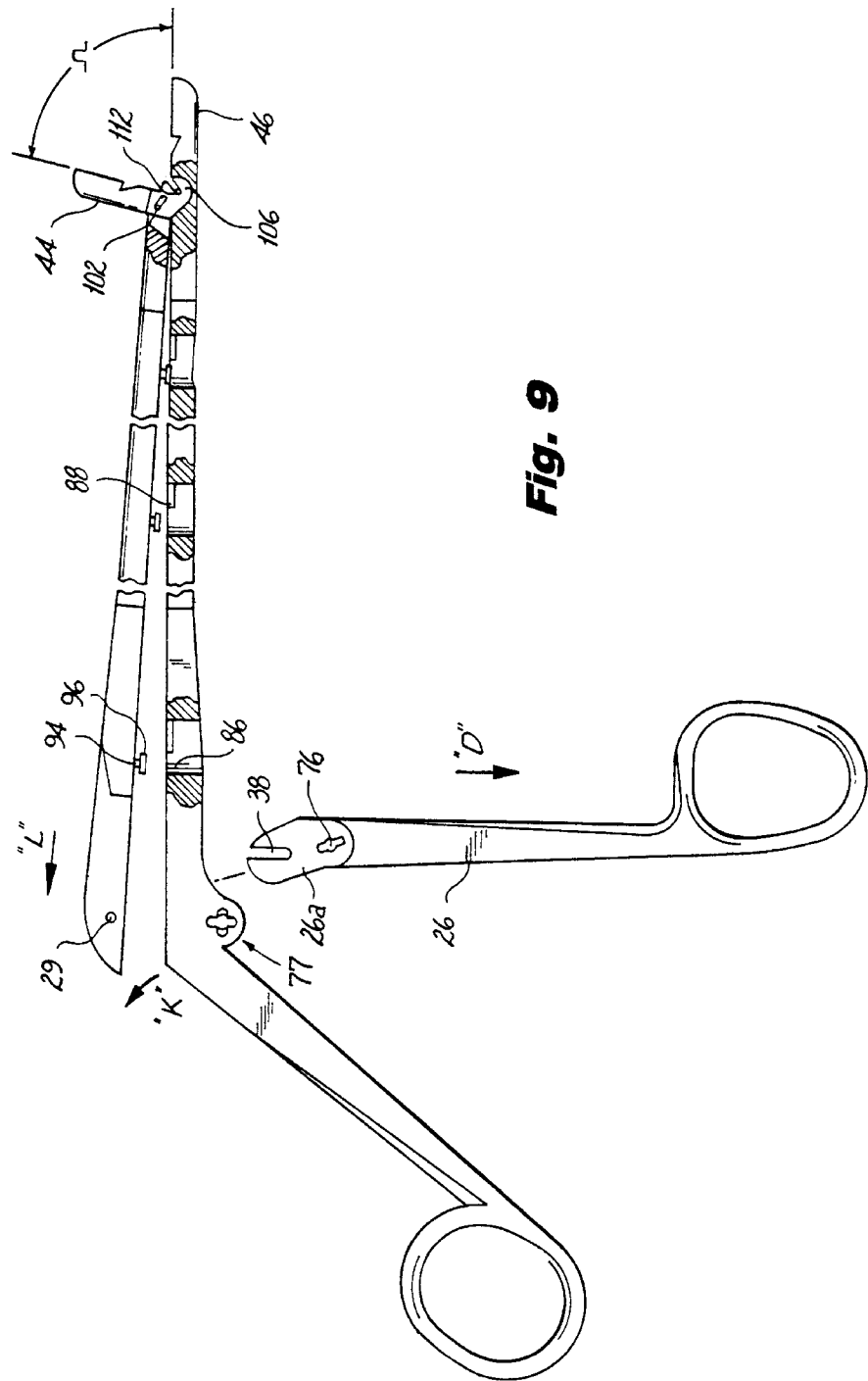
FIG. 9 is a side plan view in partial cross section of the instrument of FIG. 1 in a third position for disassembly.

As seen in FIG. 2, pivotable grip 26 is pivotally and detachably connected to lower body portion 22b by locking member 28 and is also pivotally mounted within upper body portion 22a. Pivotable grip 26 is pivotable about pivot pin 29 which is disposed within a generally semi-circular shaped recess 36(FIG. 7) formed in upper body portion 22a. Pivot pin 29 is preferably formed integrally within upper portion 22a, but alternatively may be attached thereto in any suitable manner, for example, by drilling a hole through upper portion 22a and inserting pin 29 therethrough. Pivotable grip 26 includes slot 38 disposed at a first end 26a thereof. First end 26a extends through tapered cutout 27 formed in lower body portion 22b such that slot 38 is received within recess 36 and engages pivot pin 29. Movement of pivotable grip 26 therefore causes first end 26a to pivot about pivot pin 29 within recess 36, thereby producing reciprocal movement of second half section member 34 as seen in FIGS. 7–9.

Figure 3:
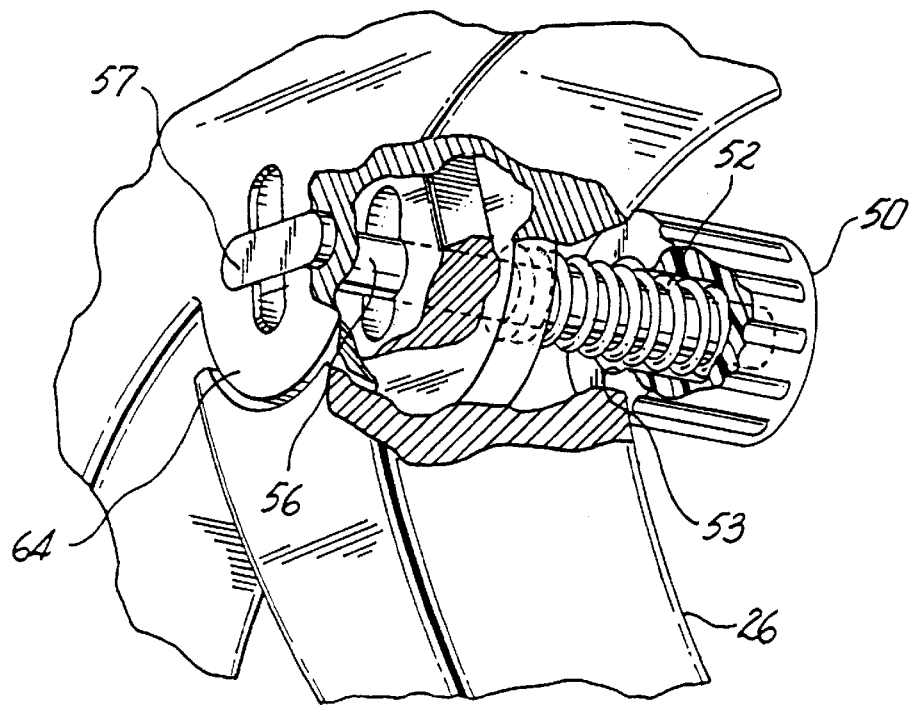
FIG. 3 is an enlarged view in partial cross-section of the locking member of FIG. 1.

Referring now to FIGS. 2–5, locking member 28 includes knob 50 and fastener 54. Fastener 54, includes a rod 56, an abutment portion 57 and is preferably of a "T" shape configuration. Fastener 54 is configured to be received through a bore 76 formed within first end 26a of pivotable grip 26, and is also received within an extension member 61 which extends from and is preferably formed integral with body portion 22. Extension member 61 includes left and right extension arms 62, 64, respectively which have an opening 66 formed therebetween. As seen in FIG. 3, when instrument 10 is assembled, rod 56 of fastener 54 extends through the left and right extension arms 62, 64 and pivotable grip 26. Rod 56 also extends from and is at least partially received within channel 53 formed in knob 50. Rod 56 is attached to knob 50 by a pin 58 (FIG. 2) which extends into knob 50 and through aperture 60 formed in rod 56. Knob 50 is biased in a direction away from body portion 22 by a compression spring 52 which is disposed circumferentially about rod 56. Compression spring 52 is received at least partially within channel 53 and is in abutment with an outer surface 70 of left extension arm 62. In the assembled position of FIG. 3, abutment portion 57 rests in shelf 78 (FIG. 4A) of engagement section 77. Engagement section 77 includes shelf portion 78 in an outer surface 80 of right extension arm 64, and further includes an elongated through-hole 82 extending through right extension arm 64 and preferably intersecting shelf portion 78 at approximately a 90 degree angle. Elongated through-hole 82 is configured to receive abutment portion 57 and is preferably a similar shape as abutment portion 57.

Figure 4A:
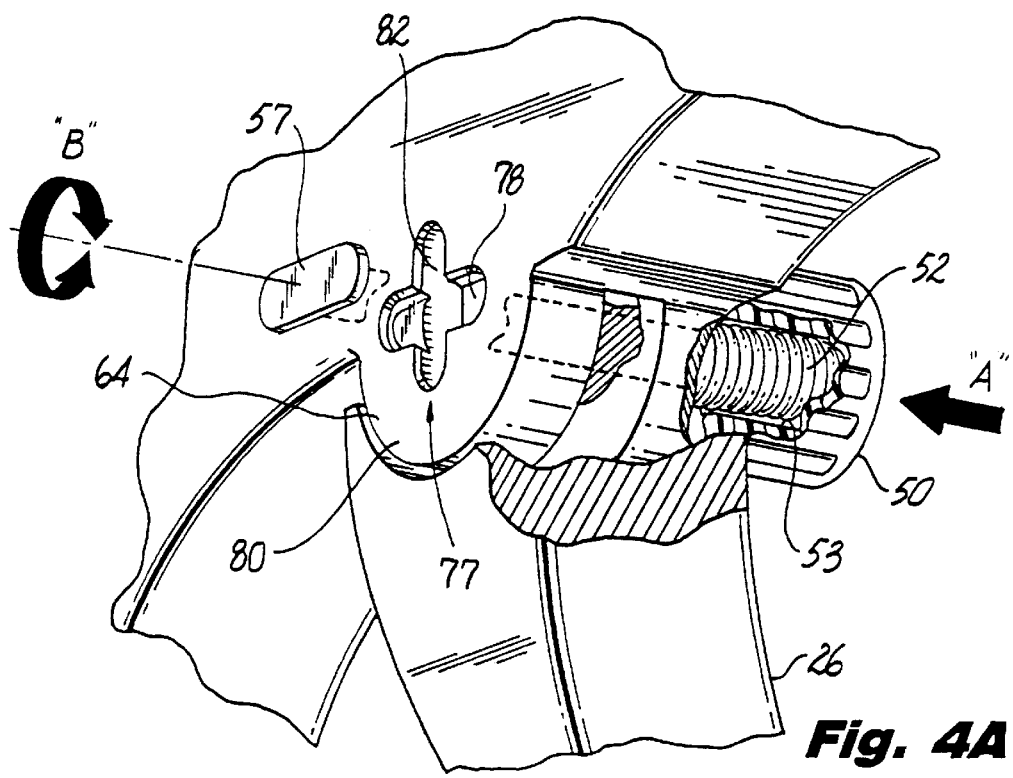
FIG. 4A is an enlarged view in partial cross-section of the locking member of FIG. 1 showing actuation of the locking member for removal of the pivotable grip from the surgical instrument of FIG. 1.
Figure 4B:
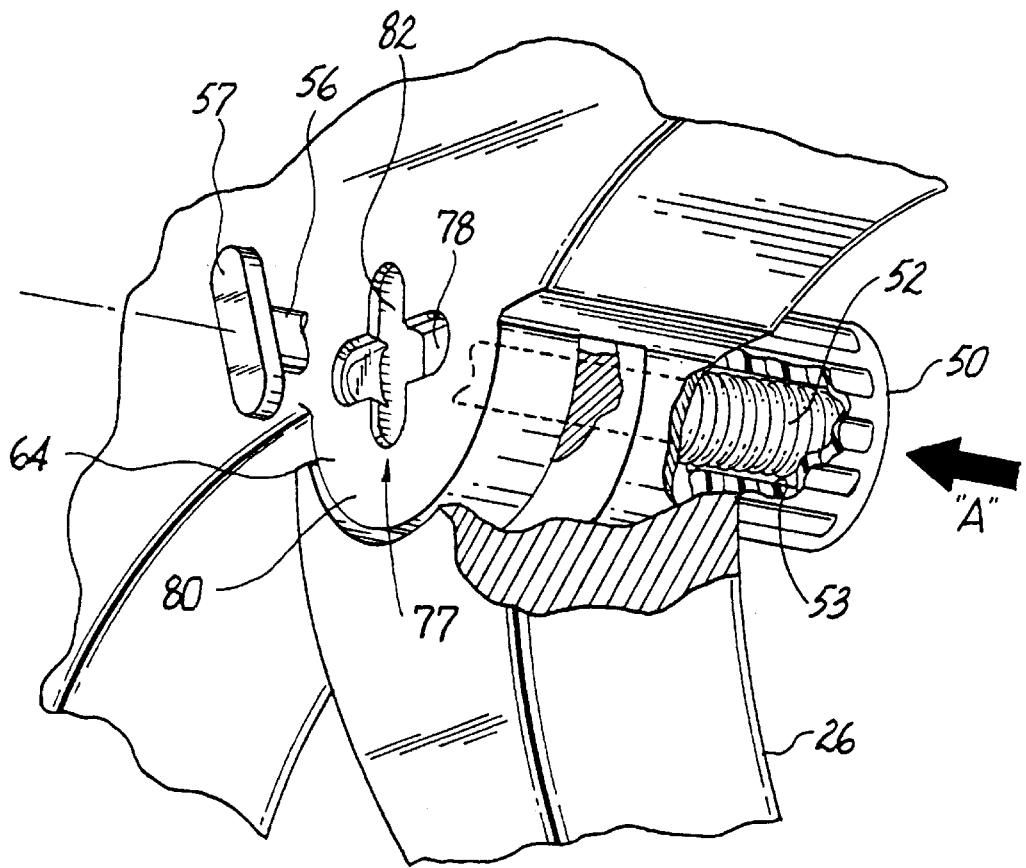
FIG. 4B is an enlarged view in partial cross-section of the locking member of FIG. 1 showing actuation of the locking member for removal of the pivotable grip from the surgical instrument of FIG. 1.

In order to detach pivotable grip 26 from body portion 22, locking member 28 must be disengaged. As shown in FIG. 4A, to disengage locking member 28 from pivotable grip 26, knob 50 is urged in the direction of arrow "A" by the user, against the biasing force of compression spring 52. Urging knob 50 in the direction of arrow "A" causes corresponding movement of fastener 54 in the direction of arrow "A" which results in abutment portion 57 being displaced from shelf portion 78. After abutment portion 57 has been displaced from shelf portion 78, knob 50 is rotated in either a clockwise or counter-clockwise direction as represented by arrow "B", approximately 90 degrees, until abutment portion 57 is in the position shown in FIG. 4B, in substantial alignment with elongated through-hole 82.

Figure 5:
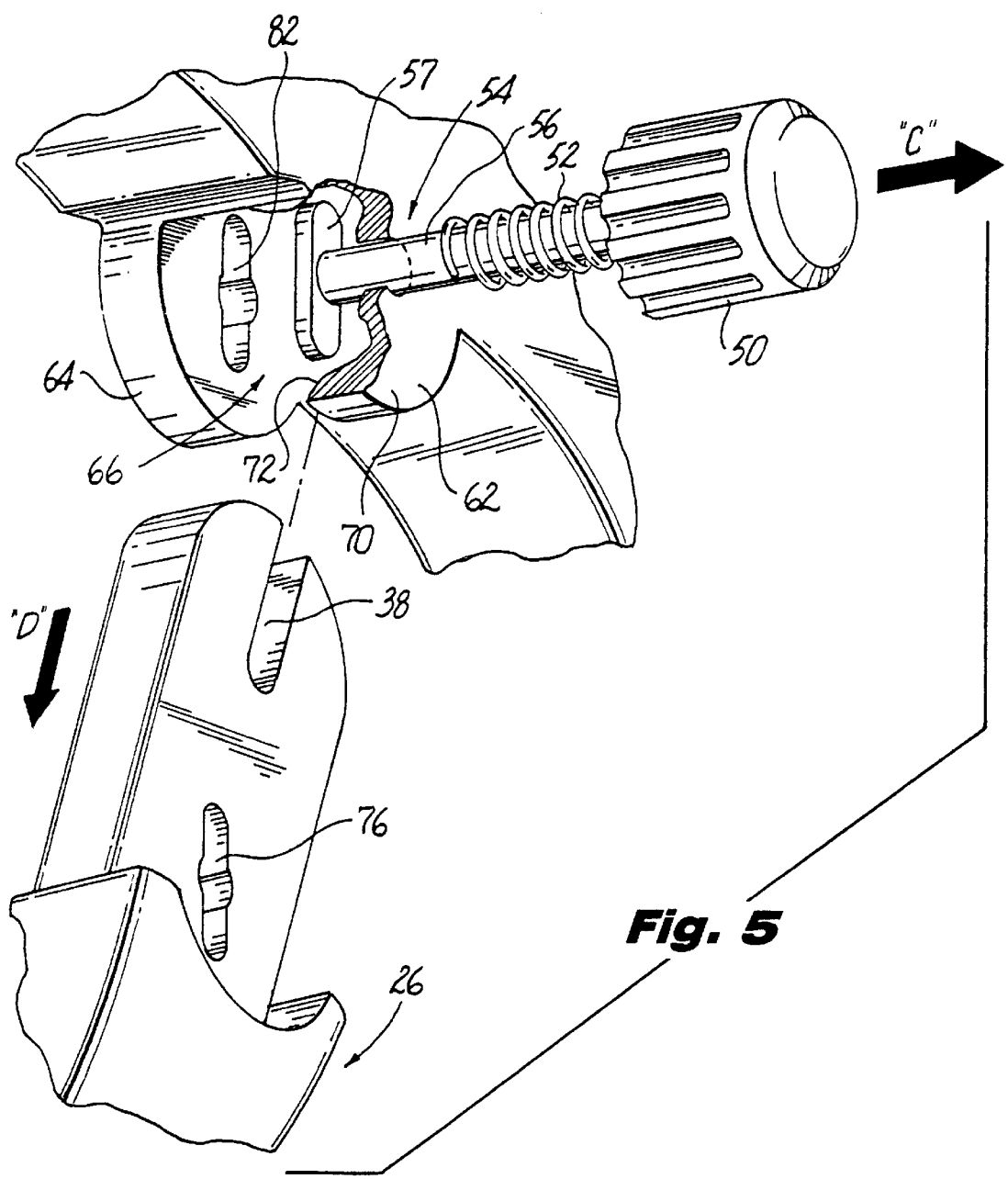
FIG. 5 is an enlarged view in partial cross-section of the locking member of FIG. 1 showing removal of the pivotable grip from the surgical instrument of FIG. 1.

Referring now to FIG. 5, once abutment portion 57 is in substantial alignment with through-hole 82, knob 50 is urged in the direction of arrow "C" thereby causing corresponding movement of fastener 54 in the direction of arrow "C". Movement of fastener 54 in the direction of arrow "C" results in abutment portion 57 and rod 56 being moved through right actuation arm 64, via through-hole 82 and into opening 66, thereby disengaging fastener 54 from right actuation arm 64. Continued movement of knob 50 in the direction of arrow "C" causes abutment portion 57 and rod 56 to travel through bore 76 formed within first end 26a of pivotable grip 26, thereby disengaging fastener 54 from engagement with pivotable grip 26. Disengagement of fastener 54 from pivotable grip 26 allows the user to move pivotable grip 26 in the direction of arrow "D" thereby releasing pivotable grip 26 from body portion 22. After fastener 54 has been disengaged from pivotable grip 26, abutment portion 57 is retained within opening 66 within a shelf (not shown) of a similar configuration to shelf 78, formed within inner surface 72 of left extension arm 62.

Referring now to FIGS. 1, 2 and 6A–6C, endoscopic portion 30 includes first-half section member 32 and second half-section member 34. Second half-section member 34 includes an outer surface 34a which preferably has a substantially semi-circular shape and a generally flat inner surface 34b. Inner surface 34b includes a plurality of inwardly projecting guide pins 94 having end members 96 which are dimensioned to cooperatively engage corresponding guide slots 84 formed in first half-section member 32, to ensure proper alignment of the first and second half-section members 32, 34 and to permit reciprocal motion of second half-section member 34 with respect to first half-section member 32 while also preventing disengagement of second half-section member 34 from first half-section member 32. Extending from and preferably formed integrally with distal end 31b of second-half section member 34 is actuation portion 98 which includes aperture 100 disposed therethrough. Pin 102 is received and secured within aperture 100 and is also slidably disposed within camming slot 104 of pivoting jaw member 44. Pivoting jaw member 44 includes arm 106 preferably formed integrally therewith. Arm 106 is received within generally semi-circular shaped slot 110 formed adjacent the distal end of first half-section member 32. Arm 106 includes aperture 108 formed therein for receipt of pivot pin 112 which extends through aperture 114 disposed adjacent the distal end of first half-section member 32.

First half-section member 32 includes an outer surface 32a which preferably has a substantially semi-circular shape and a generally flat inner surface 32b which includes a plurality of guide slots 84 formed therein. Guide slots 84 each include a first section 86, preferably of a generally oval configuration having a width "w" which is preferably greater than the width of end members 96. Guide slots 84 also each include a second section 88 in communication with the first section 86 also preferably having a generally oval configuration. Section 88 includes stepped portion 89 which includes a lower portion 91 also having a width "w" and an upper portion "93" having a width "w1" which is preferably smaller than the width of end members 96. Therefore, when assembling instrument 10, guide pins 94 and end members 96 are inserted into first section 86 and then slidably moved in a proximal direction such that end members 96 are disposed and retained within lower portion 91 of stepped portion 89. Extending from and preferably formed integrally with distal end 31a of first-half section member 32 is stationary jaw member 46. Jaw member 46 includes cup section 90 for grasping and removing portions of tissue during an endoscopic discetomy procedure and further includes "V" shaped cutouts 92a and 92b for enhancing the gripping of tissue.

The operation of instrument 10 will now be described with reference to FIGS. 7–9. In use, instrument 10 is inserted into the surgical site via a trocar assembly (not shown) preferably in the position shown in FIG. 7. In this position pivotable grip 26 is in a first position with respect to stationary grip 24 and tool mechanism 40 is in an initial position in which jaw member 44 is substantially parallel with respect to jaw member 46. In the position of FIG. 7 slot 38 is in engagement with pivot pin 29 as described hereinabove and guide pins 94 along with end members 96 are disposed in second sections 88 of guide slots 84. Once in position at the surgical site, the user may move pivotable handle in the direction of arrow "F" into a second position (FIG. 8) thereby urging second half-section member 34 in a proximal direction as represented in the drawing by arrow "G". As second half-section member 34 moves proximally it causes corresponding movement of guide pins 94 along with end members 96 within second section 88 of guide slots 84 to the position shown in FIG. 8. Movement of second half-section member 34 in the proximal direction also urges pin 102 proximally which causes pin 102 to ride in camming slot 104 in the direction of arrow "H". As pin 102 rides in camming slot 104 in the direction of arrow "H", arm 106 is pivoted about pin 112 within slot 110 (FIG. 2) and pivoting jaw member 44 is thereby pivoted in the direction of arrow "I" into an open position at an angle μ with respect to stationary jaw member 46 (FIG. 8). Pivotable grip 26 has a range of motion which is limited by walls 27a and 27b of preferably tapered cutout 27, therefore, second-half section member 34 in unable to be moved beyond a predetermined proximal position thereby restraining pivoting jaw member 44 from pivoting beyond angle μ which preferably does not exceed approximately 45 degrees.

With continuing reference to FIGS. 7–9, when instrument 10 is to be disassembled, pivotable grip 26 is first detached from body portion 22 by disengaging locking member 28 as described hereinabove. After pivotable grip 26 is removed in the direction of arrow "D", second half-section member 34 is able to be moved proximally beyond the predetermined proximal position, in the direction represented by arrow "L". As second half-section member 34 moves proximally it causes guide pins 94 along with end members 96 to be moved into first sections 86 of guide slots 84. Movement of second half-section member 34 also causes pivoting jaw member 44 to open at an angle Ω with respect to stationary jaw member 46, which is greater than angle μ. When guide pins 94 along with end members 96 are moved into first sections 86, second half-section member 34 may be disengaged from first half-section 32 by lifting second half-section member 34 in the direction of arrow "K" and by disengaging pin 102 from camming slot 104.

To assemble instrument 10, pin 102 is inserted into camming slot 104 and guide pins 94 and end members 96 are inserted into first section 86. Guide pins 94 and end members 96 are then moved in a proximal direction such that end members 96 are retained within lower portion 91 of stepped portion 89. First end 26a of pivotable handle 26 is then inserted through tapered cutout 27 and into recess 36 such that slot 38 of first end 26 engages pivot pin 29. Knob 50 is then moved against the force of biasing spring 52 to insert fastener 54 through bore 76 formed within first end 26a of pivotable grip 26 and also through extension member 61, knob 50 is then rotated until abutment portion 57 rests within shelf portion 78.

Figure 10:
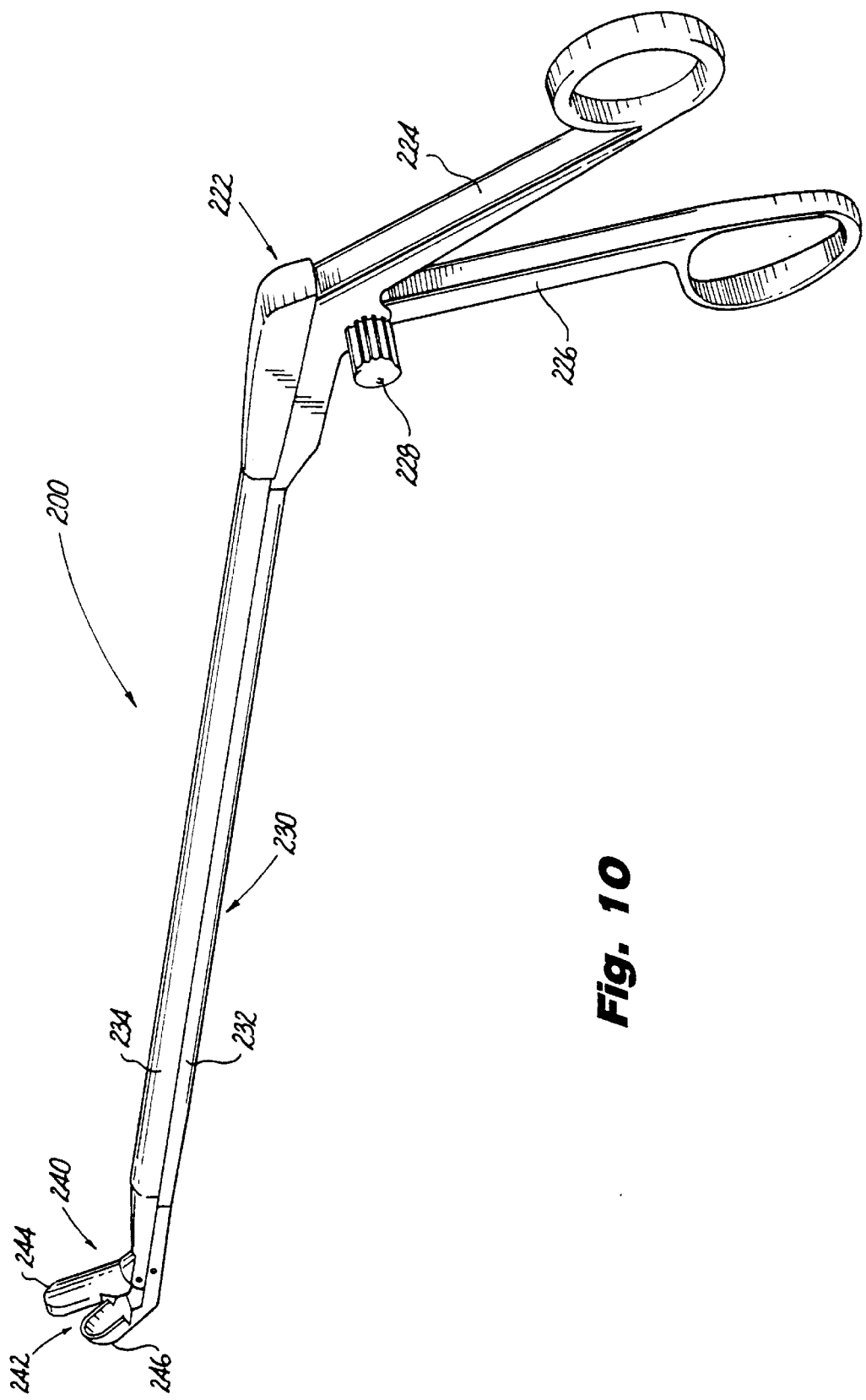
FIG. 10 is a perspective view of an alternate embodiment of the instrument of FIG. 1 having an angled jaw mechanism.
Figure 13:
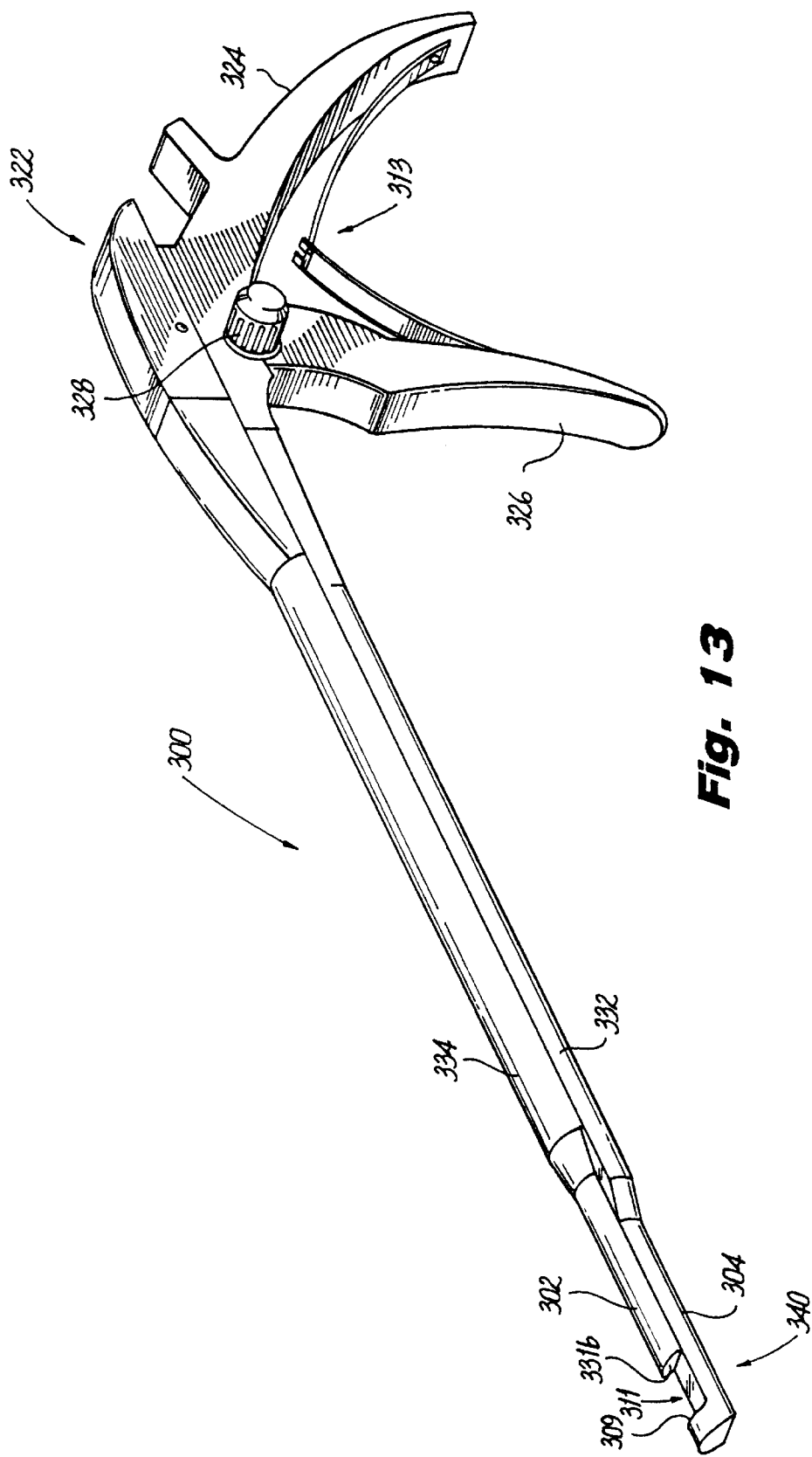
FIG. 13 is a perspective view of an alternate embodiment of an endoscopic surgical instrument for use during an endoscopic discectomy procedure according to the present application.
Figure 14:
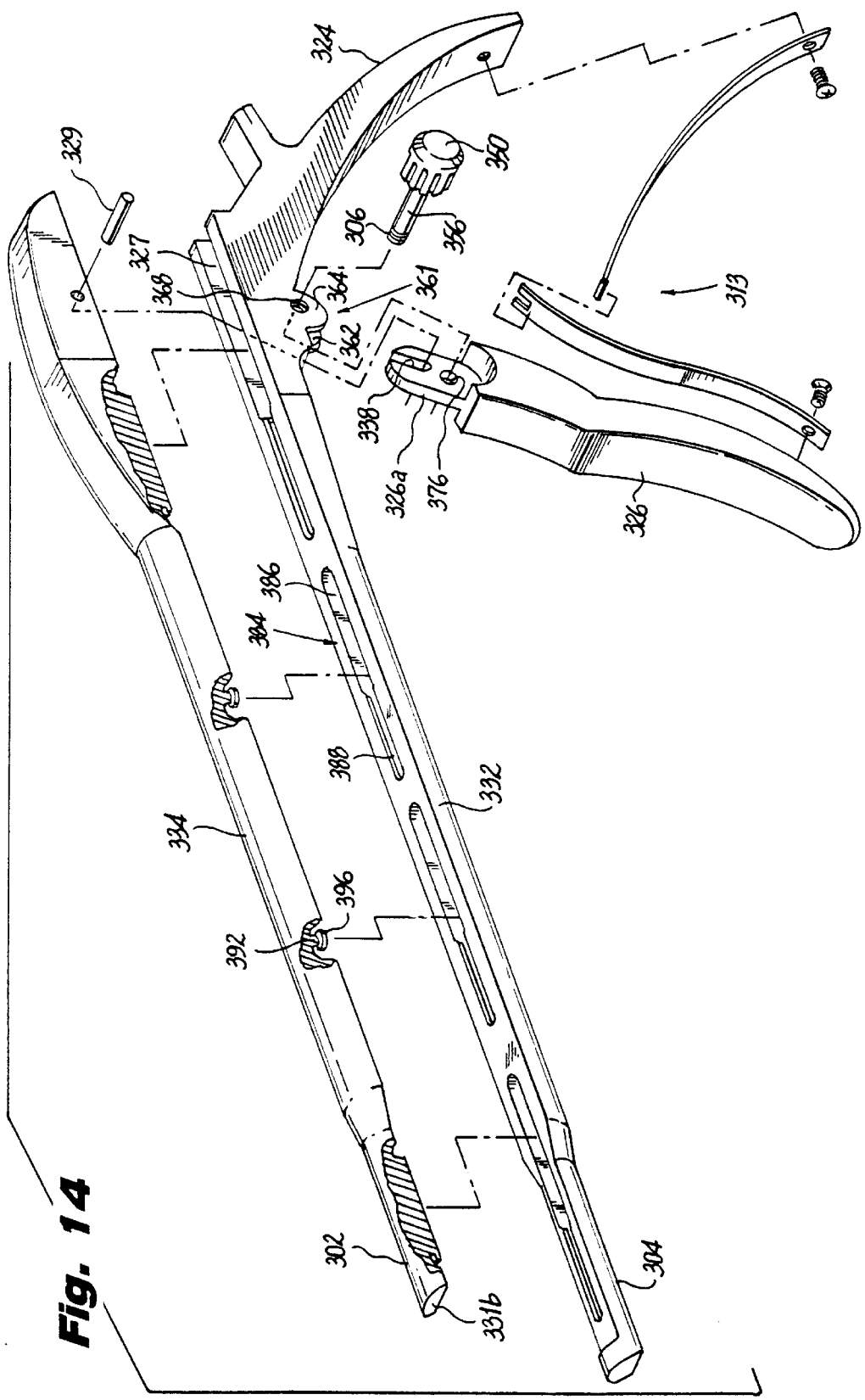
FIG. 14 is a perspective view with parts separated of the surgical instrument of FIG. 13.
Figure 15:
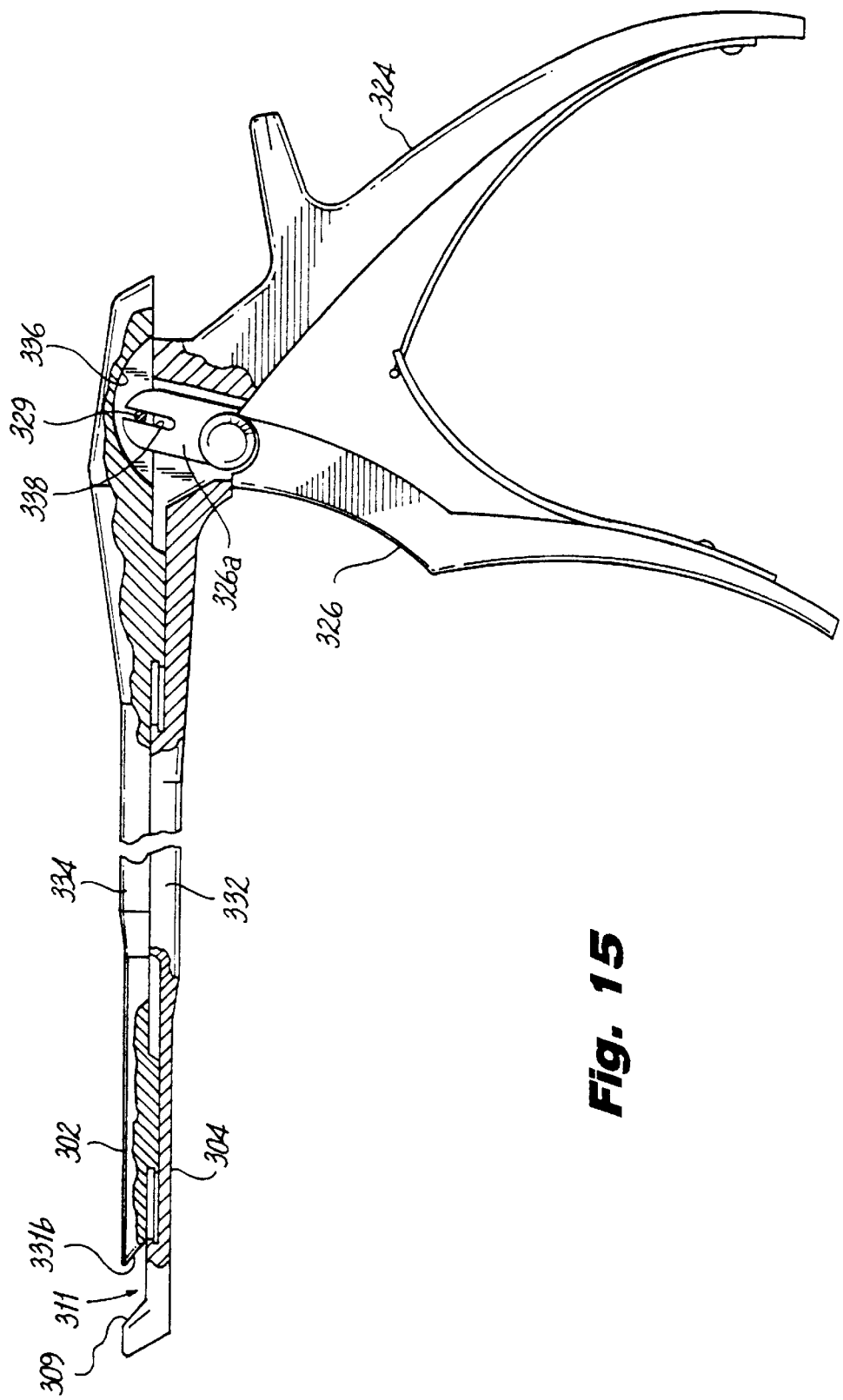
FIG. 15 is a side plan view in partial cross section of the instrument of FIG. 13 in a first position.
Figure 16:
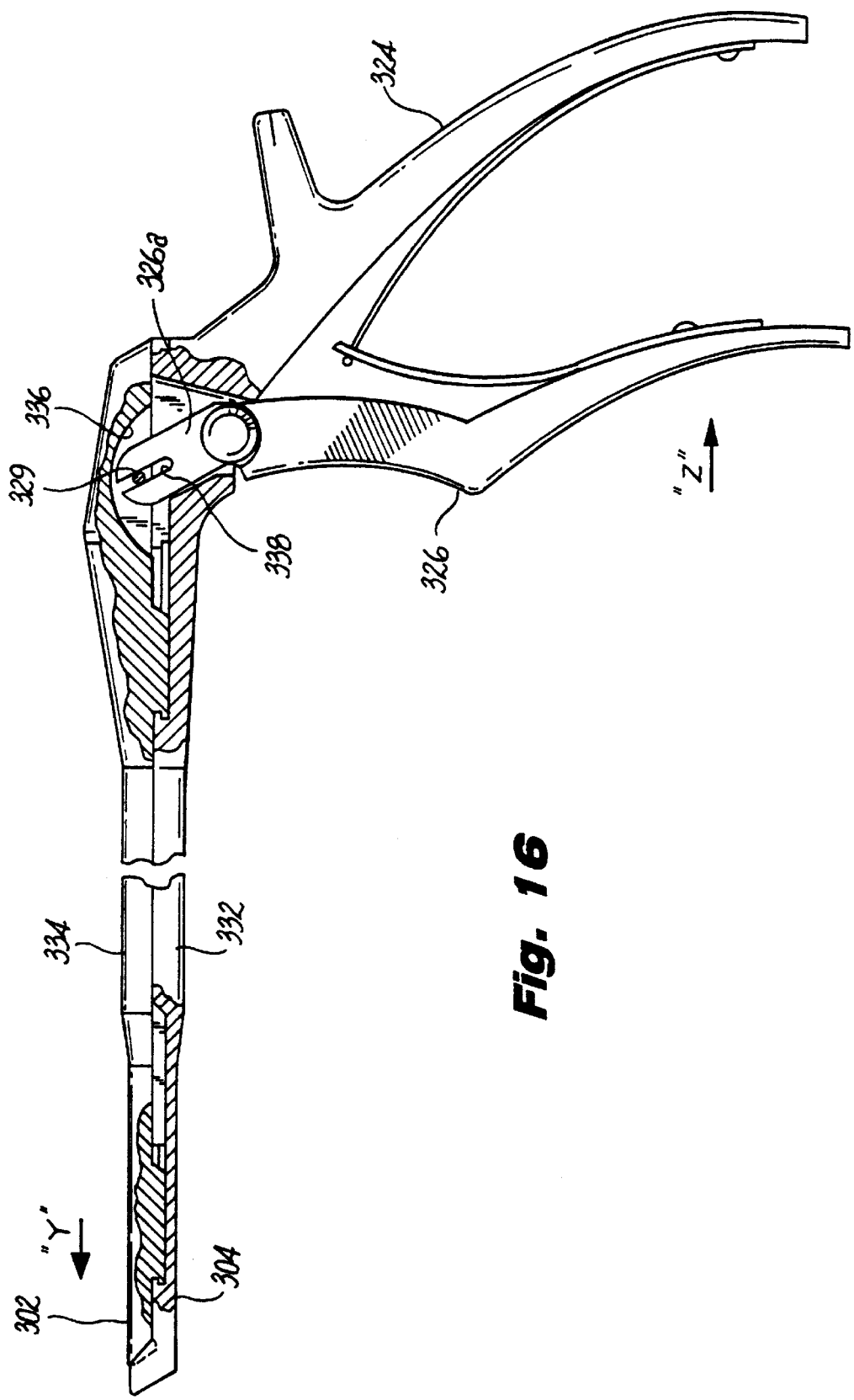
FIG. 16 is a side plan view in partial cross section of the instrument of FIG. 13 in a second actuated position.

Referring now to FIGS. 10–12, there is illustrated an alternate embodiment of an instrument according to the present application. Instrument 200 is substantially similar to instrument 10 except that jaw assembly 242 includes an angled actuating jaw member 244 and an angled stationary jaw member 246. Angled jaw members 244 and 246 operate in the same fashion as jaw members 44 and 46, but are angularly disposed with respect to endoscopic portion 30 at all times.

Turning now to FIGS. 13–16, there is illustrated an endoscopic surgical rongeur instrument 300 which may be used to trim away part of a bone during an endoscopic discectomy procedure and which is configured to be disassembled for cleaning and reassembled for subsequent utilization. Instrument 300 is similar to instrument 10 except that tool mechanism 340 includes an upper actuating shaft 302 and a lower stationary shaft 304. Actuating shaft 302 extends from and is preferably formed integral with second half-section member 334 while lower stationary shaft 304 extends from and is preferably formed integral with first half-section member 332. Stationary shaft 304 includes angular engagement section 309 which cooperates with a distal end 31b of actuation shaft 302. Second half-section member 334 is preferably removably mounted to the first half-section member 32 and is slidable with respect thereto as described hereinabove with respect to the embodiment of FIG. 1; except that locking member 328 in the embodiment of FIG. 13 includes knob 350 and rod 356 which is preferably formed integrally there with and includes a threaded portion 306 which is an alternative to abutment portion 57 of FIG. 1.

Rod 356 is configured to be received through internally threaded bore 376 formed within first end 326a of pivotable grip 326, and is also received within an extension member 361 which extends from and is preferably formed integral with body portion 322. Extension member 361 includes left and right extension arms 362, 364, respectively which have an opening 366 (not shown) formed therebetween. Extension arms 362, 364 each included an internally threaded bore 368 for receipt of rod 356. When instrument 300 is assembled, rod 356 extends into the left and right extension arms 362, 364 and pivotable grip 326.

In operation, a piece of bone which is to be removed is placed in gap 311 formed between angular engagement section 309 and distal end 331b of actuation shaft 302. Pivotable grip 326 is then moved in the direction of arrow "Z" by the user which causes second half-section member 334 to move distally in the direction of arrow "Y" relative to first half-section member 332, as described hereinabove with respect to FIG. 1. Movement of second half-section member 334 causes corresponding movement of actuating shaft 302 in the direction of arrow "Y" thereby crushing any bone disposed in gap 311 against angular engagement section 309. Disposed between pivotable grip 326 and stationary grip 324 is a biasing spring 313 which acts to return pivotable grip 326 to the first position shown in FIG. 13 when pivotable grip 326 is released by the user.

Instrument 300 is disassembled in a similar manner as described hereinabove with reference to FIG. 1. Disassembly of second half-section member 334 from first half-section member 332 is accomplished by first disengaging spring 313, unscrewing rod 356 from extension member 361 and internally threaded bore 376. Pivotable handle 326 is then removed from body assembly 322 and second half-section member 334 is moved proximally until guide pins 394 and end members 396 extending from second half-section member 334 are be moved into first sections 386 of guide slots 384 formed within first half-section member 332 as described hereinabove with respect to the embodiment of FIG. 1. Second half-section member 334 is then lifted from engagement with first half-section member 332.

What is claimed is:

1. An endoscopic surgical instrument adapted to be readily disassembled to facilitate sterilization of component parts, which comprises:

a handle including a frame and an actuating grip moveable relative to the frame, the actuating grip being detachably mounted to the frame;

an elongated endoscopic portion extending from the handle and defining a longitudinal axis, the endoscopic portion including a first stationary portion and a second movable portion detachably mounted to the first stationary portion, the endoscopic portion having an outer arcuate dimension defined by arcuate outer surfaces of the first stationary portion and the second moveable portion;

connecting means for operatively connecting the first and second portions such that in an operative mode the second movable portion is in mounting engagement with the first stationary portion and is adapted for longitudinal linear movement relative to the first stationary portion between a first proximal position and a second distal position in response to movement of the actuating grip, in a non-operative mode with the actuating grip removed from the frame, the second movable portion is in mounting engagement with the first stationary portion and is further longitudinally moveable relative to the first stationary portion to a release position, and at the release position the second movable portion is capable of being detached from the first stationary portion to permit disassembly of the endoscopic portion, the first stationary portion and the second movable portion having cooperating inner contacting surfaces correspondingly configured and dimensioned such that during longitudinal linear movement of the second movable portion between the first proximal position and the second distal position egress of gas through the endoscopic portion is minimized, the connecting means associated with the inner contacting surfaces of the first stationary portion and the second moveable portion, and being contained within the outer arcuate dimension of the endoscopic portion; and a tool mechanism operatively associated with a distal end portion of the endoscopic portion and movable in response to movement of the second movable portion.

2. The endoscopic surgical instrument according to claim 1, wherein the handle includes a release mechanism for detachably mounting the actuating grip to the frame, the release mechanism including a rotatable knob and a locking rod fixedly connected to the rotatable knob, the rotatable knob and locking rod rotatable to a release position to permit release of the actuating grip from the frame.

3. The endoscopic surgical instrument according to claim 2, wherein the actuating grip is pivotably mounted about the locking rod.

4. The endoscopic surgical instrument according claim 3, wherein the locking rod is receivable within corresponding apertures formed in the frame and the actuating grip to mount the actuating grip.

5. The endoscopic surgical instrument according to claim 4, wherein the locking rod is slidably moveable within the apertures of the frame and the actuating grip and is removable through the apertures of the frame and the actuating grip upon rotation of the locking rod to the release position thereby permitting removal of the actuating grip from the frame.

6. The endoscopic surgical instrument according to claim 4, wherein the locking rod includes a threaded portion, the threaded portion threadably engageable with a threaded bore of the frame to releasably mount the actuating grip.

7. The endoscopic surgical instrument according to claim 2, further including a spring member disposed about at least a portion of the locking rod and engageable with the rotatable knob for biasing the rotatable knob outwardly away from the frame.

8. The endoscopic surgical instrument according to claim 1, wherein the second movable portion of the endoscopic portion includes at least two guide pins extending from the inner planar surface thereof, the two guide pins receivable within correspondingly dimensioned slots formed in the inner planar surface of the first stationary portion to slidably mount the second movable portion and limit vertical and lateral movement of the second movable portion to further minimize the egress of gas through the endoscopic portion.

9. The endoscopic surgical instrument according to claim 1, wherein the release position of the second movable portion is proximal of the first proximal position.

10. The endoscopic surgical instrument according to claim 9 wherein the slots formed in the other of the first stationary portion and the second movable portion include proximal slot portions dimensioned to permit passage of the two guide pins therethrough wherein in the release position of the second movable portion the second movable portion can be lifted from the first stationary portion to facilitate disassembly thereof.

11. The endoscopic surgical instrument according to claim 1, wherein the tool mechanism includes a jaw structure having first and second jaw members, the first jaw member being detachably mounted to the second jaw member.

12. The endoscopic surgical instrument according to claim 11, wherein at least the first jaw member is pivotally mounted about a pivot pin and movable between an open position and a closed position in response to movement of the second movable portion of the endoscopic portion, the pivot pin extending through corresponding apertures in the first and second jaw members.

13. The endoscopic surgical instrument according to claim 12, wherein the pivot pin is removable through the apertures of the first and second jaw members to permit detachment of the first jaw member from the second jaw member.

14. The endoscopic surgical instrument according to claim 13, wherein the jaw structure includes a camming mechanism for moving the first jaw member between the open and closed positions, the camming mechanism including a camming slot and a camming pin positioned within the camming slot.

15. The endoscopic surgical instrument according to claim 1, wherein the tool mechanism includes cutting structure for severing tissue, the cutting structure including a cutting edge defined at the distal end of the second movable portion and an engagement surface defined at a distal end of the first stationary portion wherein tissue positioned between the cutting edge and the engagement surface is severed upon distal movement of the second movable portion.

16. The endoscopic surgical instrument according to claim 1, including a biasing spring associated with the actuating grip for biasing the actuating grip to an open position.

17. The endoscopic surgical instrument according to claim 1 wherein the cooperating contacting surfaces of the first stationary portion and the second movable portion are inner planar surfaces.

18. A surgical rongeur, which comprises:
a handle assembly, including:
a frame;
a movable grip; and
a quick release mechanism for pivotably and releasably mounting the movable grip to the frame, the quick release mechanism including a rotatable knob and a locking rod fixedly connected to the rotatable knob and having an enlarged locking head, opposite to the rotatable knob the locking rod and the locking head configured to be received within corresponding apertures formed in the frame and the movable grip such that the movable grip is pivotal about the locking rod, the locking rod having a non threaded outer surface such that the rotatable knob and the locking rod are rotatable to a release position to permit sliding removal of the locking rod and the locking head from the apertures and removal of the movable grip from the frame; and
an elongated endoscopic portion extending from the handle assembly and defining a longitudinal axis, the endoscopic portion including a stationary portion and a movable portion releasably mounted to the stationary portion and longitudinally movable relative to the stationary portion between a first proximal position and a second distal position in response to pivotal movement of the movable grip, the stationary portion including an engagement surface defined at a distal end thereof, the movable portion including a cutting surface defined at a distal end thereof cooperating with the engagement surface to sever tissue, the movable portion being further movable from the first proximal position to a release position subsequent to removal of the movable grip from the frame to permit the movable portion to be released from the stationary portion, the movable portion being in mounting engagement with the stationary portion during movement from the first proximal position to the release position.

19. The surgical rongeur according to claim 18, wherein the release position of the movable portion is located proximal of the first proximal position.

20. The endoscopic surgical instrument of claim 18 wherein the locking rod is received within corresponding apertures defined in the frame and the pivoting grip and is slidably moveable within the apertures, wherein upon rotation of the locking rod to the release position thereof the locking rod may be removed from the handle by sliding movement of the locking rod through the apertures of the frame and the pivoting grip.

21. The endoscopic surgical instrument according to claim 18 wherein the movable portion of the endoscopic portion includes at least two guide pins extending from an inner surface thereof, the two guide pins receivable within correspondingly dimensioned slots formed in the stationary portion to slidably mount the movable portion to the stationary portion.

22. The endoscopic surgical instrument according to claim 21 wherein the slots formed in the stationary portion include proximal slot portions dimensioned to permit passage of the two guide pins therethrough wherein in the release position of the movable portion the movable portion may be lifted from the stationary portion to facilitate disassembly thereof.

23. An endoscopic surgical instrument which comprises:
a handle including a frame and a pivoting grip pivotally mounted to the frame about a releasable locking rod, the locking rod received within corresponding apertures defined in the frame and the pivoting grip, and being slidably moveable within the apertures, the locking rod having an enlarged locking head, the enlarged locking head being configured to pass through the apertures such that when the locking head is passed through the apertures and rotated, the locking rod is in a secured position;

an elongated endoscopic portion extending from the frame of the handle and defining a longitudinal axis, the endoscopic portion including a stationary portion and a movable portion in mounted engagement with the stationary portion and adapted for longitudinal reciprocal substantially linear movement relative to the stationary portion between a first proximal position and a second distal portion in response to pivotal movement of the pivoting grip, the stationary portion being substantially semi-circular in cross-section and having a substantially planar inner surface, the moveable portion being semi-circular in cross-section and having a substantially planar inner surface cooperating with the substantially planar inner surface of the stationary portion to minimize egress of gas through the endoscopic portion, the movable portion being further movable to a release position proximal of the first proximal position upon release of the pivoting grip from the frame to permit removal of the movable portion from the stationary portion, the movable portion being in mounted engagement with the stationary portion during movement to the release position; and a tool mechanism operatively associated with a distal end portion of the endoscopic portion and actuable in response to movement of the movable portion.

24. An endoscopic surgical instrument, which comprises:
a handle including a frame and an actuating member pivotally mounted to the frame about a releasable locking rod, the locking rod having a knob and an enlarged locking head opposite to the knob, the locking head being configured to be slidably received within corresponding apertures defined in the frame and the actuating member such that passage of the locking rod through the apertures and subsequent rotation thereof causes the locking head to engage one of the frame and the actuating member to secure the locking rod in a secured position;

an elongated portion extending from the frame of the handle and defining a longitudinal axis and having proximal and distal end portions, the elongated portion including a movable member operatively connected to the actuating member grip and movable between an initial position and an actuated position upon movement of the actuating member; and a tool mechanism operatively associated with the movable member of the elongated portion and actuable upon movement of the movable member to the actuated position.

* * * * *